US012579774B2

(12) United States Patent
Dhariwal et al.

(10) Patent No.: US 12,579,774 B2
(45) Date of Patent: Mar. 17, 2026

(54) SYSTEM AND METHOD FOR AUTOMATIC TAGGING OF IMAGES AND VIDEO IN AN OPERATIVE REPORT

(71) Applicant: VAIM Technologies LLC, Oceanport, NJ (US)

(72) Inventors: Manjeet Dhariwal, Victor, NY (US); Aaron Feiler, Fair Haven, NJ (US); Inderpal Singh Sarkaria, Dallas, TX (US)

(73) Assignee: VAIM TECHNOLOGIES LLC, Oceanport, NJ (US)

(*) Notice: Subject to any disclaimer, the term of this patent is extended or adjusted under 35 U.S.C. 154(b) by 420 days.

(21) Appl. No.: 18/133,293

(22) Filed: Apr. 11, 2023

(65) Prior Publication Data

US 2023/0326172 A1    Oct. 12, 2023

Related U.S. Application Data

(60) Provisional application No. 63/329,921, filed on Apr. 12, 2022.

(51) Int. Cl.

| | |
|---|---|
| *G06V 10/42* | (2022.01) |
| *G06V 10/70* | (2022.01) |
| *G10L 15/02* | (2006.01) |
| *G10L 15/06* | (2013.01) |
| *G10L 15/22* | (2006.01) |
| *G10L 15/26* | (2006.01) |
| *G10L 25/57* | (2013.01) |
| *G16H 15/00* | (2018.01) |

(52) U.S. Cl.

CPC .............. *G06V 10/42* (2022.01); *G06V 10/70* (2022.01); *G10L 15/02* (2013.01); *G10L 15/063* (2013.01); *G10L 15/22* (2013.01);

*G10L 15/26* (2013.01); *G10L 25/57* (2013.01); *G16H 15/00* (2018.01); *G06V 2201/03* (2022.01)

(58) Field of Classification Search
None
See application file for complete search history.

(56) References Cited

U.S. PATENT DOCUMENTS

| | | | | |
|---|---|---|---|---|
| 2017/0132785 A1* | 5/2017 | Wshah | .................. | G06T 7/0012 |
| 2021/0133972 A1* | 5/2021 | Ngo Dinh | ............ | A61B 5/7264 |
| 2022/0207896 A1* | 6/2022 | Fouts | ................... | G06V 10/454 |
| 2023/0298589 A1* | 9/2023 | Madan | .................... | G10L 15/22 |
| | | | | 704/9 |
| 2024/0161497 A1* | 5/2024 | Luengo Muntion | ..... | G06N 3/08 |

FOREIGN PATENT DOCUMENTS

CN        110517756 A  * 11/2019  ............... H04N 7/18

* cited by examiner

*Primary Examiner* — David Ometz

(74) *Attorney, Agent, or Firm* — ROSSI, KIMMS & McDOWELL LLP

(57) ABSTRACT

Systems and methods for automatically extracting one or more salient images from a surgical video stream are described. A plurality of records including annotated images from recorded surgical procedures are used as training data to generate an image extraction machine learning model. Features, extracted from the training data, are used as inputs to the image extraction machine learning model in a training phase, which outputs salient images. After training, features extracted from the surgical video stream are input into the trained image extraction machine learning model to output the one or more salient images from the surgical video stream.

18 Claims, 14 Drawing Sheets

900

```
910 ─┐  Receive video of
         surgical procedure
            │
920 ─┐  Receive transcription   1050 ─┐ Speech ML model
         of user speech
            │
930 ─┐  Identify keyword in     1150 ─┐ Video and image ML
         transcription using              model
         ML model
            │
940 ─┐  Extract video and
         images using
         keyword or ML
         model
            │
950 ─┐  Generate operative
         record using
         transcription and
         tagged video and
         images
```

100

130 — MEMORY DEVICE SYSTEM

110 — DATA PROCESSING DEVICE SYSTEM

120 — INPUT-OUTPUT DEVICE SYSTEM

200

210

AI/ML Driven NLP Dictation

220

Video Capture & Logs

250

Integrated UI

240

Surgeon Quality Assessment

230

Operative Record Creation

INDIVIDUAL PREFERENCES
AND CUSTOMIZATION

FIG. 4

OPERATIVE WORKFLOW

FIG. 5A

OPERATIVE WORKFLOW

FIG. 5B

OPERATIVE WORKFLOW

OPERATIVE WORKFLOW

FIG. 5D

Final Simulation Run Operative Report

600

| | |
|---|---|
| Patient Name | Robert Smith |
| MRN | 11860 |
| Date of Birth | 1969-11-03 |
| Date of Surgery | 2020-09-02, 17:26:13 |
| Attending Surgeon (Primary) | Jonathan J. |
| Name of Procedure | Robotic thymectomy |
| Pre Operative Diagnosis | Thymoma |
| Post Operative Diagnosis | Same |
| Anesthesia | General endotracheal anesthesia with double lumen tube intubation |
| First Assistant | Dr. Inderpal |
| Additional Assistants | Karan |
| Estimated Blood Loss | 50 ml |
| Specimen | Radical thymectomy |

Operative Findings

Full discussion of risks, benefits, and rationale of the intended procedure was conducted with the patient prior to proceeding to the or.and informed consent signed.
The tumor appeared to be well encapsulated within the final surgical specimen with no evidence of extra thymic invasion.

Operative Procedure

The patient was brought to the operative suite and their identity confirmed. The patient was placed on the operative table in the supine position and all pressure points padded. Serial compression devices were placed on the lower extremities.
After induction of general endotracheal anesthesia, appropriate access and monitoring lines were placed by the anesthesia team. A double lumen bronchial blocker was placed and its position confirmed with fiberoptic bronchoscopy. Left lung isolation was instituted.
Ports were removed under direct vision. A single 24f chest was placed in the left chest, and an 8f pigtail catheter in the right chest. These were placed on 20mmhg water seal to a pleurevac. The lung was expanded under direct vision and all port sites and wounds closed in the usual fashion with vicryl for the deep layers and monocryl for the skin. Steri-strips and sterile dressings were applied. The patient was awakened from anesthesia, extubated, and taken to the recovery room in good condition.

Operative Images

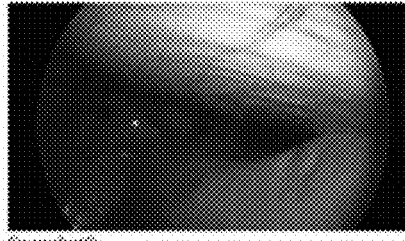
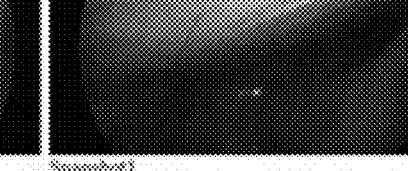

Snapshot0    Snapshot1

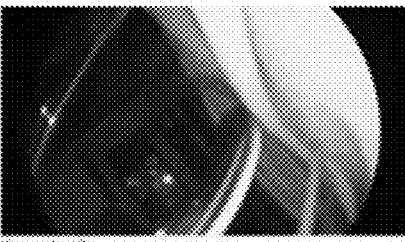

Snapshot2

FIG. 6

| | |
|---|---|
| Dictated By | Jonathan J. |
| Transcribed Date/Time | 2020-09-02, 17:33 |

800

810 — Receive video of surgical procedure

820 — Receive transcription of user speech

1050 — Speech ML model

830 — Identify keyword in transcription

840 — Tag video based on identified keyword

850 — Generate operative record using transcription and tagged video

900

1000

1100

SYSTEM AND METHOD FOR AUTOMATIC TAGGING OF IMAGES AND VIDEO IN AN OPERATIVE REPORT

TECHNICAL FIELD

Aspects of this document relate generally to systems and methods for automatic tagging of images and video in a surgical stream for keyboard-less generation and summarization of surgical operative report, and more particularly to a combination of AI-driven natural language and image processing systems for dictation, voice recognition, and image and video capture for synchronously generating and assessing operative records during surgical procedures.

BACKGROUND

An operative report is a report written in a patient's medical record to document the details of a surgery. Conventionally, the operative report is dictated right after a surgical procedure and later transcribed into the patient's record. The information in the operative report includes preoperative and postoperative diagnosis and the condition of the patient after the surgery. It is necessary for other healthcare professionals immediately attending the postoperative recovery of the patient.

The operative report is produced by a surgeon or other physician(s) who have participated in the surgery and contains a detailed account of the findings, the procedure used, the specimens removed, and the preoperative and postoperative diagnoses. The operative report may also include identifying information of the patient and names of the primary performing surgeon and any assistants. In the medicolegal context, the operative report serves to document the steps that were and were not taken to complete the surgery without unintended injury. As lawsuits and trials occur years after surgery when memories have faded, a well written operative report detailing the steps taken to avoid surgical complication is crucial to a successful defense, as it allows the defendant to reconstruct a surgery performed years earlier. It is very important that the operative report describes the steps taken in chronological order.

Surgeons typically document operative events using dictation services. Dictated reports are frequently incomplete or delayed. Certain elements must be included to ensure that the operative report satisfies institutional and national standards. After transcribing, the surgeon must review, correct errors, and ultimately "verify" the dictated report. There may be delays to the time of initial dictation by the surgeon, transcription of the dictated report, or final verification by the surgeon. Delays or lack of structure in dictation may also increase the likelihood that important elements may be missing from the final report.

Tagged multimedia—images and video clips of the surgery—form a very important part of the operative report. They provide critical evidence required to reconstruct what happened during a surgical procedure. Conventionally, a surgeon has to review the entire surgical video, which could be hours long, after surgery and manually tag or insert salient images or video clips into the operative report. Not only is this process time consuming, it is error-prone and puts the onus for accuracy and completeness on the surgeon.

Accordingly, a need in the art exists for improved automatic generation of operative reports including automatically extracting and tagging salient images or video clips of the surgical procedure.

SUMMARY

At least the above-discussed need is addressed, and technical solutions are achieved in the art by various embodiments of the present invention. In some embodiments, a system for automatic extraction of one or more salient images from a surgical video stream comprises one or more computer accessible-storage devices configured to store instructions and one or more processors communicatively connected to the one or more computer accessible storage devices and configured to execute the stored instructions to receive a plurality of records including annotated images from recorded surgical procedures to use as training data for generating an image extraction machine learning model; extract one or more first features from the training data; generate the image extraction machine learning model, by training the image extraction machine learning model on the extracted one or more first features, to output salient images in the training data; receive the surgical video stream; extract one or more second features from the surgical video stream; and input the one or more second features into the trained image extraction machine learning model to output the one or more salient images from the surgical video stream.

In some embodiments, the system is further configured to automatically generate a surgical operative record including at least the extracted one or more salient images from the surgical video stream.

In some embodiments, the system is further configured to receive a plurality of annotated speech samples to use as training data for generating a speech transcription machine learning model; extract one or more third features from the training data; generate the speech machine learning model, by training the speech machine learning model on the extracted one or more third features, to output a speech transcription; receive an audio stream associated with the surgical video stream; extract one or more fourth features from the audio stream; input the one or more fourth features into the trained speech machine learning model to output a speech transcription of the audio stream; and associate the extracted one or more salient images with the output speech transcription.

In some embodiments, the system is further configured to automatically generate a surgical operative record including at least the one or more extracted salient images and the associated output speech transcription.

In some embodiments, a timestamp is associated with each salient image of the one or more salient images.

In some embodiments, the system is further configured to receive a plurality of records including annotated video clips from recorded surgical procedures to use as second training data for training the image extraction machine learning model; extract one or more fifth features from the second training data; train the image extraction machine learning model, using the extracted one or more fifth features, to output salient video clips in the second training data; extract one or more sixth features from the surgical video stream; and input the one or more sixth features into the trained image extraction machine learning model to output one or more salient video clips from the surgical video stream.

In some embodiments, a processor implemented method of automatically extracting salient images from a surgical video stream comprises receiving a plurality of records including annotated images from recorded surgical procedures to use as training data for generating an image extraction machine learning model; extracting one or more first features from the training data; generating the image extraction machine learning model, by training the image extraction machine learning model on the extracted one or more first features, to output salient images in the training data; receiving the surgical video stream; extracting one or more second features from the surgical video stream; and inputting the one or more second features into the trained image extraction machine learning model to output the one or more salient images from the surgical video stream.

In some embodiments, the method further comprises automatically generating a surgical operative record including at least the extracted one or more salient images from the surgical video stream.

In some embodiments, the method further comprises receiving a plurality of annotated speech samples to use as training data for generating a speech transcription machine learning model; extracting one or more third features from the training data; generating the speech machine learning model, by training the speech machine learning model on the extracted one or more third features, to output a speech transcription; receiving an audio stream associated with the surgical video stream; extracting one or more fourth features from the audio stream; inputting the one or more fourth features into the trained speech machine learning model to output a speech transcription of the audio stream; and associating the extracted one or more salient images with the output speech transcription.

In some embodiments, the method further comprises automatically generating a surgical operative record including at least the one or more extracted salient images and the associated output speech transcription.

In some embodiments, the method further comprises associating a timestamp with each salient image of the one or more salient images.

In some embodiments, the method further comprises receiving a plurality of records including annotated video clips from recorded surgical procedures to use as second training data for generating the image extraction machine learning model; extracting one or more fifth features from the second training data; training the image extraction machine learning model, using the extracted one or more fifth features, to output salient video clips in the second training data; extracting one or more sixth features from the surgical video stream; and inputting the one or more sixth features into the trained image extraction machine learning model to output one or more salient video clips in the surgical video stream.

In some embodiments, an operative record generation system comprises one or more computer accessible-storage devices configured to store instructions and one or more processors communicatively connected to the one or more computer accessible storage devices and configured to execute the stored instructions to provide a plurality of program modules including a user interface, a speech processing module, an image processing module, and a record generation module.

The user interface is configured to display a video of the surgical procedure in a first portion of a screen and a transcription of a user's speech in a second portion of the screen. The speech processing module is configured to identify one or more predetermined keywords in the transcription, each keyword associated with a particular function executed by the operative record generation system. The image processing module is configured to, in a case where the speech processing module identifies a keyword associated with an image capture or video capture function, record an image or a portion of the video of the operation displayed on the screen and a timestamp associated with the recorded image or the portion of the video. The record generation module is configured to generate the operative record using the transcription of the user's speech and the recorded image or the portion of the video.

In some embodiments, the user interface further includes setting screens configured to personalize settings of the speech processing module for a user.

In some embodiments, the user interface is further configured to display an indicator indicating an active or inactive status of the operative record generation system.

In some embodiments, the speech processing module is further configured to extract the user's speech by filtering an input audio stream to remove background noise and non-user speech.

In some embodiments, the video and image processing module is further configured to receive a plurality of operative records including tagged videos and images to use as training data for generating a video and image extraction machine learning model; extract one or more features from the training data; and train the video and image extraction machine learning model, using the extracted one or more features, to automatically record an image or a portion of the video of the operation displayed on the screen and a timestamp associated with the recorded image or the portion of the video.

In some embodiments, the system further includes a speech transcription module configured to receive a plurality of transcribed and annotated speech samples to use as training data for generating a speech transcription machine learning model; extract one or more features from the training data; and train the speech machine learning model, using the extracted one or more features, to transcribe the user's speech.

In some embodiments, a method of generating an operative record inlcudes displaying, on a user interface, a video of the surgical procedure in a first portion of a screen and a transcription of a user's speech in a second portion of the screen; identifying one or more predetermined keywords in the transcription, each keyword associated with a particular function executed by the operative record generation system; in a case where a keyword associated with an image capture or video capture function is identified, recording an image or a portion of the video of the operation displayed on the screen and a timestamp associated with the recorded image or the portion of the video; and generating the operative record using the transcription of the user's speech and the recorded image or the portion of the video.

In some embodiments, the method further includes extracting the user's speech by filtering an input audio stream to remove background noise and non-user speech.

In some embodiments, the method further includes receiving a plurality of operative records including tagged videos and images to use as training data for generating a video and image extraction machine learning model; extracting one or more features from the training data; and training the video and image extraction machine learning model, using the extracted one or more features, to automatically record an image or a portion of the video of the operation displayed on the screen and a timestamp associated with the recorded image or the portion of the video.

In some embodiments, the method further includes receiving a plurality of transcribed and annotated speech samples to use as training data for generating a speech transcription machine learning model; extracting one or more features from the training data; and training the speech machine learning model, using the extracted one or more features, to transcribe the user's speech.

In some embodiments, one or more computer non-transitory storage media are configured to store one or more programs that include instructions for executing one or more of the various methods discussed above.

Various embodiments of the present invention may include methods, systems, devices, or machines that are or include combinations or subsets of any one or more of the methods, systems, devices, or machines and associated features thereof summarized above or otherwise described herein.

BRIEF DESCRIPTION OF THE DRAWINGS

Embodiments will be discussed hereafter using reference to the included drawings, briefly described below, wherein like designations refer to like elements:

FIG. 4 shows an exemplar user interface screen for the operative record generation system, according to some embodiments of the present invention;

Figure 5B:
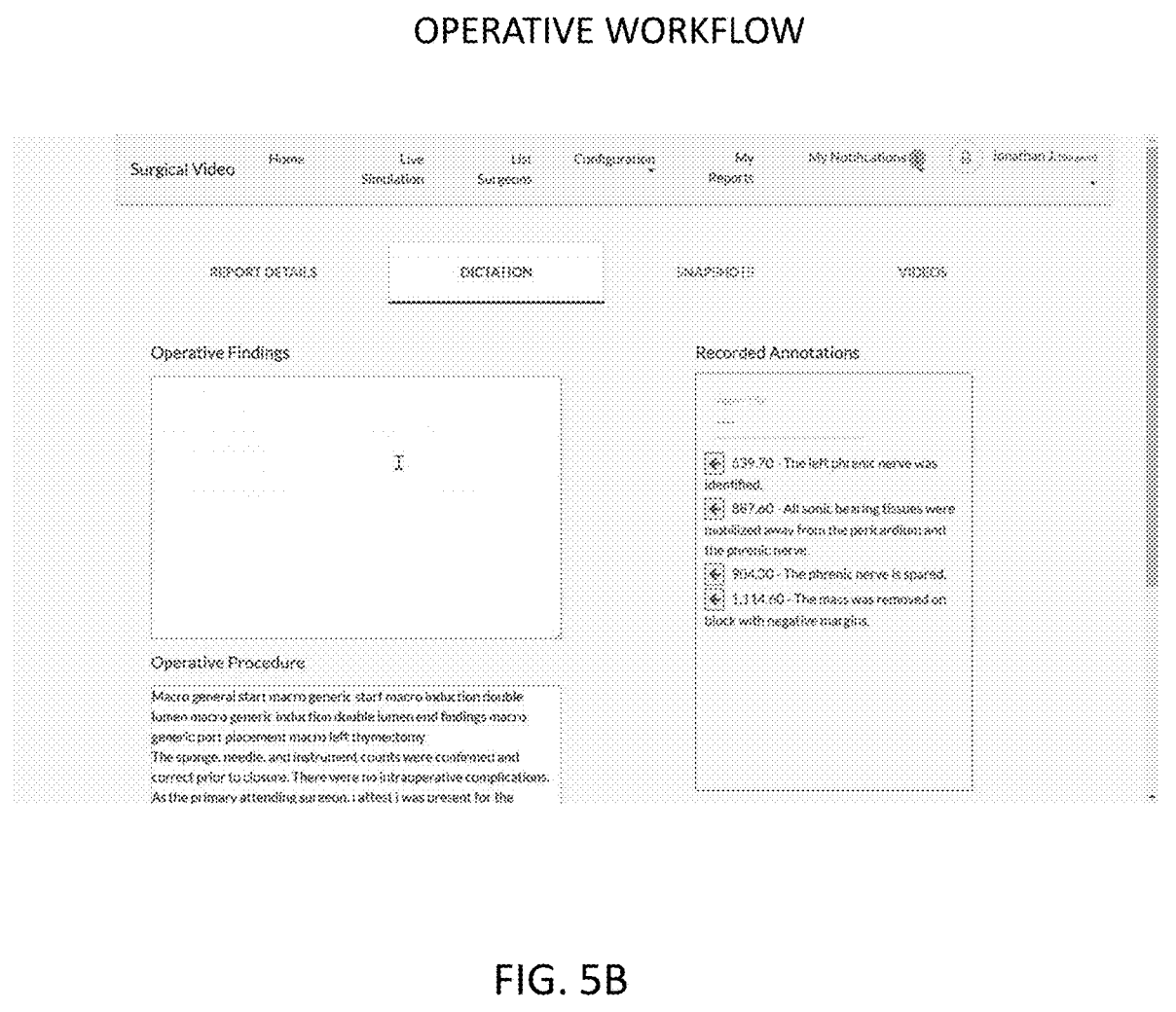

FIGS. 5A-5D shows an exemplar workflow for the operative record generation system, according to some embodiments of the present invention;

FIG. 6 shows an exemplar operative record generated by the operative record generation system, according to some embodiments of the present invention;

DETAILED DESCRIPTION

Figure 1:
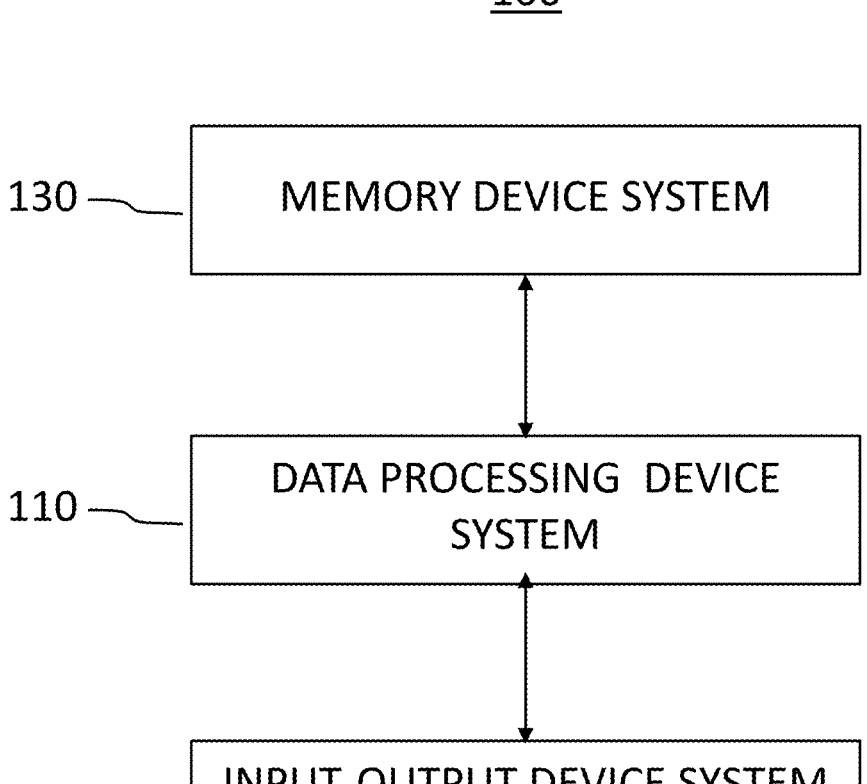
FIG. 1 shows a computing device system, according to embodiments of the invention.

Implementations/embodiments disclosed herein (including those not expressly discussed in detail) are not limited to the particular components or procedures described herein. Additional or alternative components, assembly procedures, and/or methods of use consistent with the intended systems & methods for synchronous automated generation of operative reports may be utilized in any implementation. This may include any materials, components, sub-components, methods, sub-methods, steps, and so forth.

As used herein, the term "input field" includes a "selector." For example, a button or space on a user interface in which a user may move a cursor to and click to make a selection, and a checkbox field, and other similar fields, as well as alphanumeric input fields, are all "input fields" as used herein.

In some embodiments, an operative record generation system provides synchronous summarization of an operative procedure with video and image tagging. It should be noted that the invention is not limited to these or any other examples provided herein, which are referred to for purposes of illustration only.

In this regard, in the descriptions herein, certain specific details are set forth in order to provide a thorough understanding of various embodiments of the invention. However, one skilled in the art will understand that the invention may be practiced at a more general level without one or more of these details. In other instances, well-known structures have not been shown or described in detail to avoid unnecessarily obscuring descriptions of various embodiments of the invention.

Any reference throughout this specification to "one embodiment", "an embodiment", "an example embodiment", "an illustrated embodiment", "a particular embodiment", and the like means that a particular feature, structure or characteristic described in connection with the embodiment is included in at least one embodiment. Thus, any appearance of the phrase "in one embodiment", "in an embodiment", "in an example embodiment", "in this illustrated embodiment", "in this particular embodiment", or the like in this specification is not necessarily all referring to one embodiment or a same embodiment. Furthermore, the particular features, structures or characteristics of different embodiments may be combined in any suitable manner to form one or more other embodiments.

Unless otherwise explicitly noted or required by context, the word "or" is used in this disclosure in a non-exclusive sense. In addition, unless otherwise explicitly noted or required by context, the word "set" is intended to mean one or more. For example, the phrase, "a set of objects" means one or more of the objects.

In the following description, some embodiments of the present invention may be implemented at least in part by a data processing device system configured by a software program. Such a program may equivalently be implemented as multiple programs, and some or all of such software program(s) may be equivalently constructed in hardware.

Further, the phrase "at least" is or may be used herein at times merely to emphasize the possibility that other elements may exist beside those explicitly listed. However, unless otherwise explicitly noted (such as by the use of the term "only") or required by context, non-usage herein of the phrase "at least" nonetheless includes the possibility that other elements may exist besides those explicitly listed. For example, the phrase, 'based at least on A' includes A as well as the possibility of one or more other additional elements besides A. In the same manner, the phrase, 'based on A' includes A, as well as the possibility of one or more other additional elements besides A. However, the phrase, 'based only on A' includes only A. Similarly, the phrase 'configured at least to A' includes a configuration to perform A, as well as the possibility of one or more other additional actions besides A. In the same manner, the phrase 'configured to A' includes a configuration to perform A, as well as the possibility of one or more other additional actions besides A. However, the phrase, 'configured only to A' means a configuration to perform only A.

The word "device", the word "machine", the word "system", and the phrase "device system" all are intended to include one or more physical devices or sub-devices (e.g., pieces of equipment) that interact to perform one or more functions, regardless of whether such devices or sub-devices are located within a same housing or different housings. However, it may be explicitly specified according to various embodiments that a device or machine or device system resides entirely within a same housing to exclude embodiments where the respective device, machine, system, or device system resides across different housings. The word "device" may equivalently be referred to as a "device system" in some embodiments.

Further, the phrase "in response to" may be used in this disclosure. For example, this phrase may be used in the following context, where an event A occurs in response to the occurrence of an event B. In this regard, such phrase includes, for example, that at least the occurrence of the event B causes or triggers the event A.

The phrase "derivative thereof" and the like is or may be used herein at times in the context of a derivative of data or information merely to emphasize the possibility that such data or information may be modified or subject to one or more operations. For example, if a device generates first data for display, the process of converting the generated first data into a format capable of being displayed may alter the first data. This altered form of the first data may be considered a derivative of the first data. For instance, the first data may be a one-dimensional array of numbers, but the display of the first data may be a color-coded bar chart representing the numbers in the array. For another example, if the above-mentioned first data is transmitted over a network, the process of converting the first data into a format acceptable for network transmission or understanding by a receiving device may alter the first data. As before, this altered form of the first data may be considered a derivative of the first data. For yet another example, generated first data may undergo a mathematical operation, a scaling, or a combining with other data to generate other data that may be considered derived from the first data. In this regard, it can be seen that data is commonly changing in form or being combined with other data throughout its movement through one or more data processing device systems, and any reference to information or data herein is intended to include these and like changes, regardless of whether or not the phrase "derivative thereof" or the like is used in reference to the information or data, unless otherwise required by context. As indicated above, usage of the phrase "or a derivative thereof" or the like merely emphasizes the possibility of such changes. Accordingly, the addition of or deletion of the phrase "or a derivative thereof" or the like should have no impact on the interpretation of the respective data or information. For example, the above-discussed color-coded bar chart may be considered a derivative of the respective first data or may be considered the respective first data itself.

The term "program" in this disclosure should be interpreted to include one or more programs including as a set of instructions or modules that may be executed by one or more components in a system, such as a controller system or data processing device system, in order to cause the system to perform one or more operations. The set of instructions or modules may be stored by any kind of memory device, such as those described subsequently with respect to the memory device system 130, 151, or both, shown in FIGS. 1 and 2, respectively. In addition, this disclosure may describe or similarly describe that the instructions or modules of a program are configured to cause the performance of an action. The phrase "configured to" in this context is intended to include at least (a) instructions or modules that are presently in a form executable by one or more data processing devices to cause performance of the action (e.g., in the case where the instructions or modules are in a compiled and unencrypted form ready for execution), and (b) instructions or modules that are presently in a form not executable by the one or more data processing devices, but could be translated into the form executable by the one or more data processing devices to cause performance of the action (e.g., in the case where the instructions or modules are encrypted in a non-executable manner, but through performance of a decryption process, would be translated into a form ready for execution). Such descriptions should be deemed to be equivalent to describing that the instructions or modules are configured to cause the performance of the action. The word "module" may be defined as a set of instructions. The word "program" and the word "module" may each be interpreted to include multiple sub-programs or multiple sub-modules, respectively. In this regard, reference to a program or a module may be considered to refer to multiple programs or multiple modules.

Further, it is understood that information or data may be operated upon, manipulated, or converted into different forms as it moves through various devices or workflows. In this regard, unless otherwise explicitly noted or required by context, it is intended that any reference herein to information or data includes modifications to that information or data. For example, "data X" may be encrypted for transmission, and a reference to "data X" is intended to include both its encrypted and unencrypted forms, unless otherwise required or indicated by context. However, non-usage of the phrase "or a derivative thereof" or the like nonetheless includes derivatives or modifications of information or data just as usage of such a phrase does, as such a phrase, when used, is merely used for emphasis.

Further, the phrase "graphical representation" used herein is intended to include a visual representation presented via a display device system and may include computer-generated text, graphics, animations, or one or more combinations thereof, which may include one or more visual representations originally generated, at least in part, by an image-capture device.

Further still, example methods are described herein with respect to FIGS. 8-11. Such figures are described to include blocks associated with computer-executable instructions. It should be noted that the respective instructions associated with any such blocks herein need not be separate instructions and may be combined with other instructions to form a combined instruction set. The same set of instructions may be associated with more than one block. In this regard, the block arrangement shown in method FIGS. 8-11 herein is not limited to an actual structure of any program or set of instructions or required ordering of method tasks, and such method FIGS. 8-11, according to some embodiments, merely illustrates the tasks that instructions are configured to perform, for example upon execution by a data processing device system in conjunction with interactions with one or more other devices or device systems.

Figure 2:
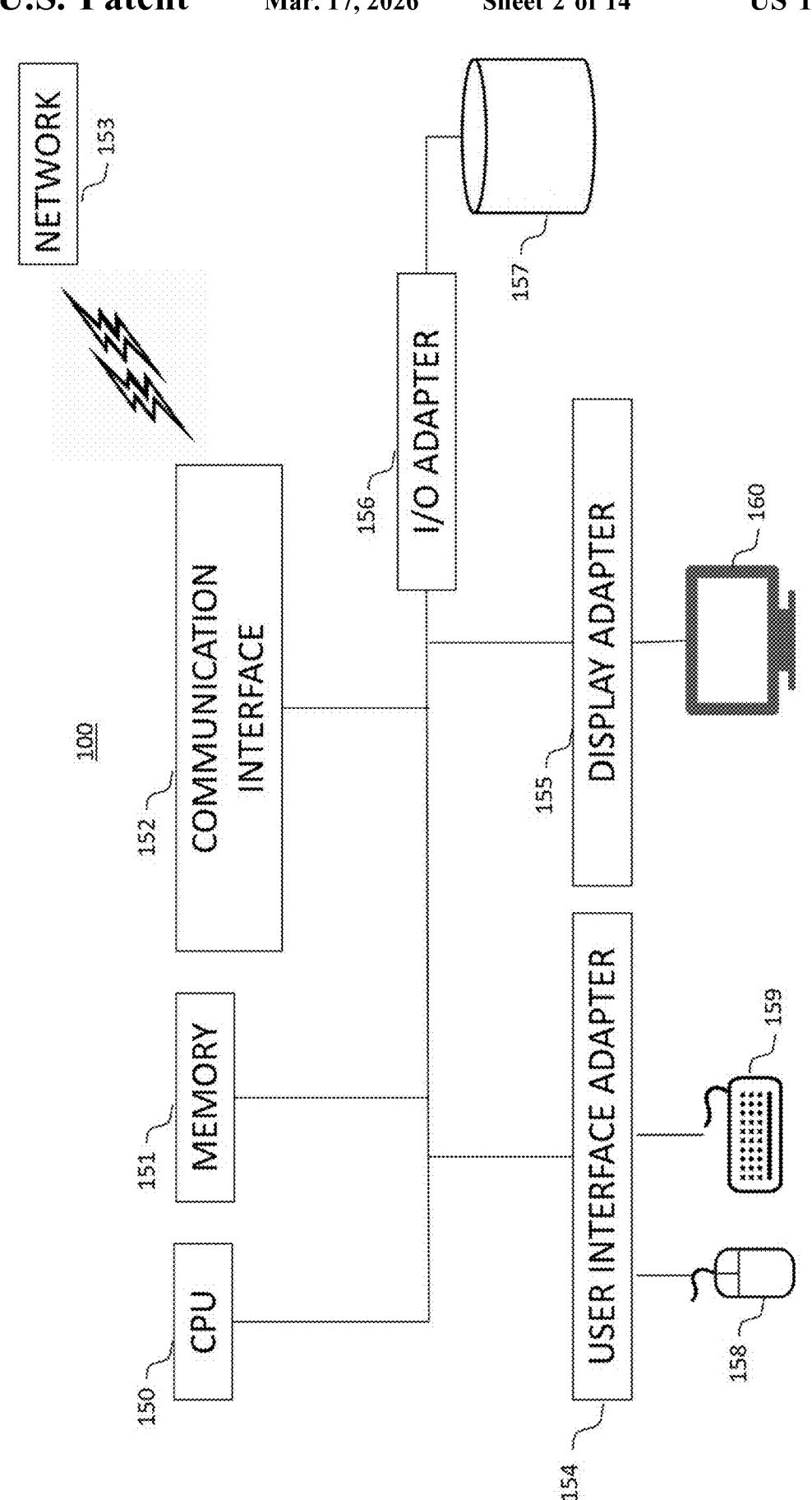
FIG. 2 shows another computing device system, according to embodiments of the invention.

FIG. 1 schematically illustrates a system 100 according to some embodiments. In some embodiments, the system 100 may be a computing device 100 (as shown in FIG. 2). In some embodiments, the system 100 includes a data processing device system 110, an input-output device system 120, and a processor-accessible memory device system 130. The processor-accessible memory device system 130 and the input-output device system 120 are communicatively connected to the data processing device system 110.

The data processing device system 110 includes one or more data processing devices that implement or execute, in conjunction with other devices, such as one or more of those in the system 100, control programs associated with some of the various embodiments. Each of the phrases "data processing device", "data processor", "processor", and "computer" is intended to include any data processing device, such as a central processing unit ("CPU"), a desktop computer, a laptop computer, a mainframe computer, a tablet computer, a personal digital assistant, a cellular phone, and any other device configured to process data, manage data, or handle data, whether implemented with electrical, magnetic, optical, biological components, or other.

The memory device system 130 includes one or more processor-accessible memory devices configured to store information, including the information needed to execute the control programs associated with some of the various embodiments. The memory device system 130 may be a distributed processor-accessible memory device system including multiple processor-accessible memory devices communicatively connected to the data processing device system 110 via a plurality of computers and/or devices. On the other hand, the memory device system 130 need not be a distributed processor-accessible memory system and, consequently, may include one or more processor-accessible memory devices located within a single data processing device.

Each of the phrases "processor-accessible memory" and "processor-accessible memory device" is intended to include any processor-accessible data storage device, whether volatile or nonvolatile, electronic, magnetic, optical, or otherwise, including but not limited to, registers, floppy disks, hard disks, Compact Discs, DVDs, flash memories, ROMs, and RAMs. In some embodiments, each of the phrases "processor-accessible memory" and "processor-accessible memory device" is intended to include a non-transitory computer-readable storage medium. In some embodiments, the memory device system 130 can be considered a non-transitory computer-readable storage medium system.

The phrase "communicatively connected" is intended to include any type of connection, whether wired or wireless, between devices, data processors, or programs in which data may be communicated. Further, the phrase "communicatively connected" is intended to include a connection between devices or programs within a single data processor, a connection between devices or programs located in different data processors, and a connection between devices not located in data processors at all. In this regard, although the memory device system 130 is shown separately from the data processing device system 110 and the input-output device system 120, one skilled in the art will appreciate that the memory device system 130 may be located completely or partially within the data processing device system 110 or the input-output device system 120. Further in this regard, although the input-output device system 120 is shown separately from the data processing device system 110 and the memory device system 130, one skilled in the art will appreciate that such system may be located completely or partially within the data processing system 110 or the memory device system 130, depending upon the contents of the input-output device system 120. Further still, the data processing device system 110, the input-output device system 120, and the memory device system 130 may be located entirely within the same device or housing or may be separately located, but communicatively connected, among different devices or housings. In the case where the data processing device system 110, the input-output device system 120, and the memory device system 130 are located within the same device, the system 100 of FIG. 1 can be implemented by a single application-specific integrated circuit (ASIC) in some embodiments.

The input-output device system 120 may include a microphone, a speaker, a mouse, a keyboard, a touch screen, another computer, or any device or combination of devices from which a desired selection, desired information, instructions, or any other data is input to the data processing device system 110. The input-output device system 120 may include any suitable interface for receiving information, instructions or any data from other devices and systems described in various ones of the embodiments.

The input-output device system 120 also may include an image generating device system, a display device system, a speaker device system, a processor-accessible memory device system, or any device or combination of devices to which information, instructions, or any other data is output from the data processing device system 110. In this regard, if the input-output device system 120 includes a processor-accessible memory device, such memory device may or may not form part or all of the memory device system 130. The input-output device system 120 may include any suitable interface for outputting information, instructions or data to other devices and systems described in various ones of the embodiments. In this regard, the input-output device system may include various other devices or systems described in various embodiments.

FIG. 2 shows an example of a computing device system 100, according to some embodiments. The computing device system 100 may include a processor 150, corresponding to the data processing device system 110 of FIG. 1, in some embodiments. The memory 151, input/output (I/O) adapter 156, and non-transitory storage medium 157 may correspond to the memory device system 130 of FIG. 1, according to some embodiments. The user interface adapter 154, mouse 158, keyboard 159, display adapter 155, and display 160 may correspond to the input-output device system 120 of FIG. 1, according to some embodiments. The computing device system 100 may also include a communication interface 152 that connects to a network 153 for communicating with other computing devices 100.

Further, it is understood that information or data may be operated upon, manipulated, or converted into different forms as it moves through various devices or workflows. In this regard, unless otherwise explicitly noted or required by context, it is intended that any reference herein to information or data includes modifications to that information or data. For example, "data X" may be encrypted for transmission, and a reference to "data X" is intended to include both its encrypted and unencrypted forms. For another example, "image information Y" may undergo a noise filtering process, and a reference to "image information Y" is intended to include both the pre-processed form and the noise-filtered form. In other words, both the pre-processed form and the noise-filtered form are considered to be "image information Y". In order to stress this point, the phrase "or a derivative thereof" or the like may be used herein. Continuing the preceding example, the phrase "image information Y or a derivative thereof" refers to both the pre-processed form and the noise-filtered form of "image information Y", with the noise-filtered form potentially being considered a derivative of "image information Y". However, non-usage of the phrase "or a derivative thereof" or the like nonetheless includes derivatives or modifications of information or data just as usage of such a phrase does, as such a phrase, when used, is merely used for emphasis.

FIGS. 8-11 include data generation and flow diagrams, which may implement various embodiments of methods 800-1100 by way of associated computer-executable instructions according to some example embodiments. In various example embodiments, a memory device system (e.g., memory device system 130) is communicatively connected to a data processing device system (e.g., data processing device systems 110, otherwise stated herein as "e.g., 110") and stores a program executable by the data processing device system to cause the data processing device system to execute various embodiments of methods 800-1100 via interaction with at least, for example, various databases. In these various embodiments, the program may include instructions configured to perform, or cause to be performed, various ones of the instructions associated with execution of various embodiments of methods 800-1100. In some embodiments, methods 800-1100 may include a subset of the associated blocks or additional blocks than those shown, respectively, in FIGS. 8-11. In some embodiments, methods 800-1100 may include a different sequence indicated between various ones of the associated blocks shown, respectively, in FIGS. 8-11.

Figure 3:
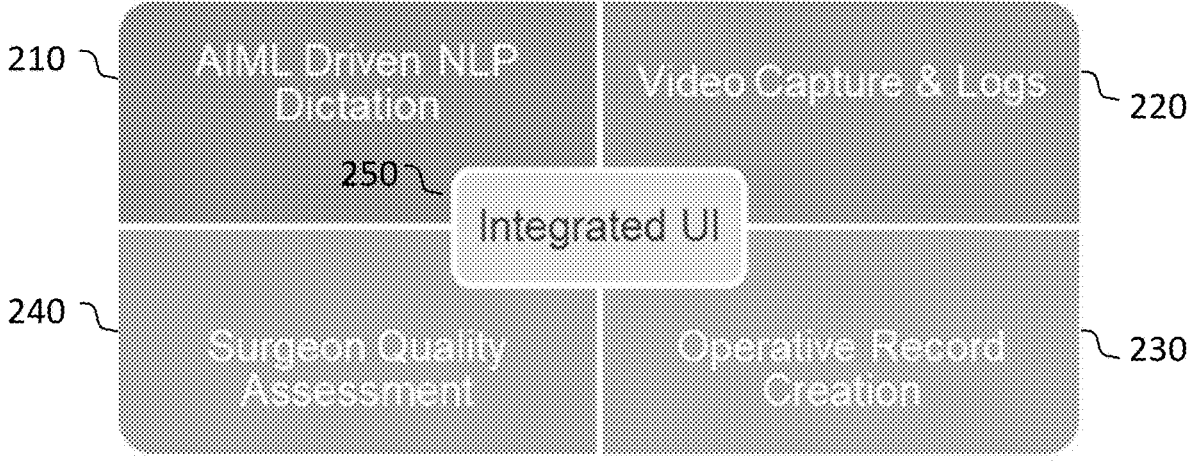
FIG. 3 shows an operative record generation system, according to some embodiments of the present invention.
Figure 5C:
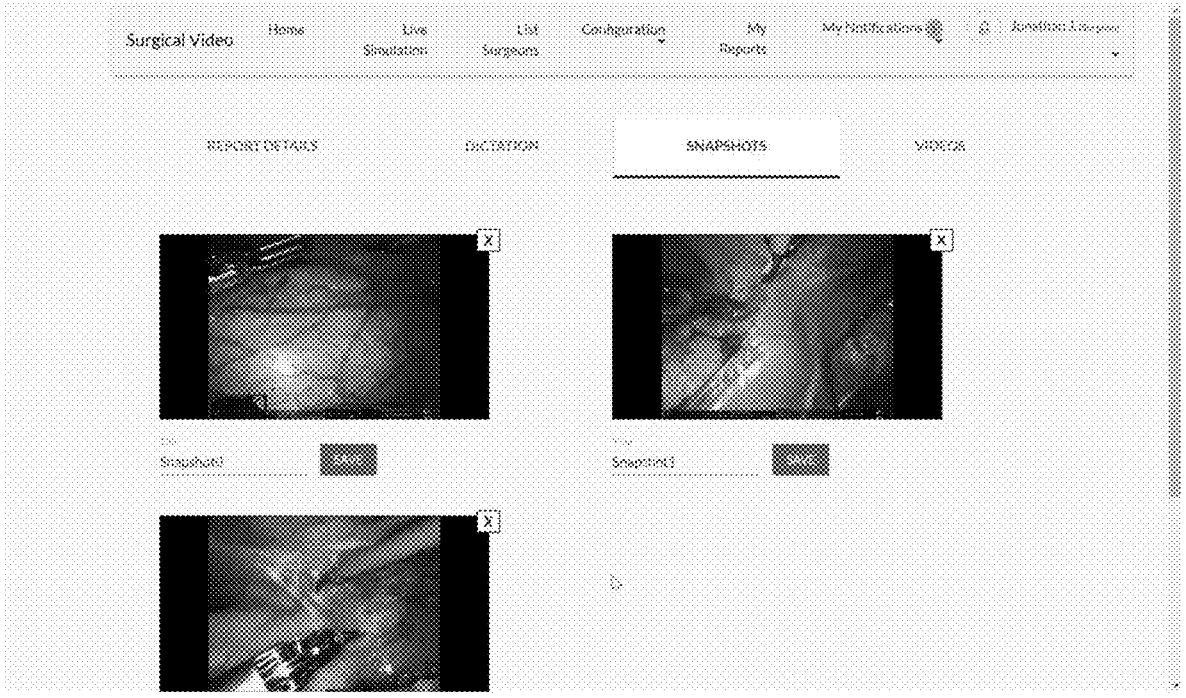

According to some embodiments of the present invention, the system 100 includes some or all of an operative record generation system 200 shown in FIG. 3, or vice versa. In this regard, FIG. 3 illustrates an operative record generation system 200, according to some embodiments of the present invention. The operative record generation system 200 may be a particular implementation of the system 100, according to some embodiments.

In some embodiments of the invention, the operative record generation system 200 includes a dictation module 210, a video and image capture logging module 220, an operative record generation module 230, a surgeon quality assessment and review module 240, and a user interface module 250. In some embodiments of the invention, the dictation module 210 is based on natural language processing methodologies and implemented using artificial intelligence and machine learning techniques. In some embodiments of the invention, video and image capture logging module 220 records video of the surgical operation, permits capturing of video frames as images, and tagging of video clips and images with descriptive information. The operative record generation module 230 captures information from the dictation module 210 and the video and image capture logging module 220 and integrates the information into an operative record 600 that can then be edited by the surgeon. This enables real-time operative record creation and editing, and the final operative record 600 can then be stored securely in the healthcare provider environment. The surgeon quality assessment module 240 enables extraction of information from the operative record 600 on a partial or a whole basis to be shared with a variety of stakeholders. An AI based scoring system is used as part of the surgeon quality assessment module 240 to determine ratings. Ratings are stored securely, and a surgeon rating report can be generated as a CSV, word, pdf or XML file, which can be printed and/or shared with other systems through defined API's.

Machine learning-based dictation processing, performed in the dictation module 210, involves using a computer program to train a speech transcription model (machine learning model) 1050, which recognizes patterns in audio recordings, to transcribe spoken words into written text. The process typically involves collecting large amounts of audio recordings to be used as training data for the speech transcription model, processing the audio recordings to extract features such as the frequency of different sounds and the duration of pauses, and training a machine learning model, such as a deep neural network, using the extracted features to recognize patterns in the audio and generate text output. The trained speech transcription model 1050 is tested on a separate dataset to evaluate its accuracy and make any necessary adjustments to ensure it is generalized. Once the speech transcription model 1050 is deemed accurate enough, it can be deployed to transcribe new audio recordings in real-time.

Figure 10:
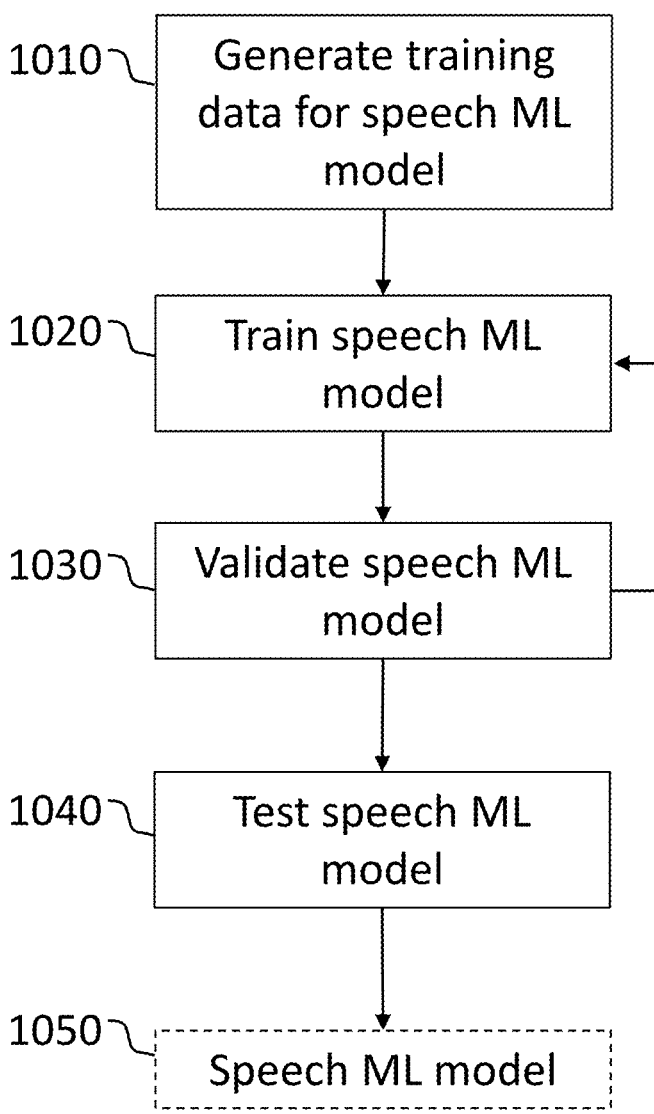
FIG. 10 shows a flowchart of a method of generating a speech machine learning model, according to some embodiments of the present invention.

FIG. 10 shows a flowchart for an exemplar method 1000 of generating the speech transcription model 1050. In the training phase, in step 1010, large amounts of audio recordings are collected and used as training data for the speech transcription model. The audio can come from various sources, such as user recordings or pre-recorded audio datasets. The audio recordings are transcribed by humans or by using other speech recognition software to create labeled datasets. In step 1020, the audio data is preprocessed to extract relevant features such as Mel-Frequency Cepstral Coefficients (MFCCs), spectrograms, and other acoustic features. A machine learning model is chosen based on the specific requirements of the application. Popular models for speech recognition include Convolutional Neural Networks (CNNs) and Recurrent Neural Networks (RNNs). The labeled audio data is used to train the selected machine learning model. The machine learning model learns from the input audio and associated transcription examples, iteratively updating its internal parameters to improve its performance.

In some embodiments, in steps 1030 and 1040, validation and testing of the trained model is performed to ensure that the model is generalized (it is not overfitted to the training data and can provide similar performance on new data as on the training data). In some embodiments, a portion of the collected training data is held back from the training set for validation (validation dataset) and testing (testing dataset). In step 1030, the validation dataset is used to estimate the trained model's performance while tuning the model's parameters to improve its accuracy. This validation step 1030 is performed iteratively with the training step 1020, to adjust the parameters of the trained model until a predetermined condition (for example, an error between the two sets being less than a predefined threshold) is met. The test dataset is used to generate an unbiased estimate of the performance of the final trained and validated model in step 1040. It is well known that evaluating the trained model using the training set would result in a biased score as the trained model is, by design, built to learn the biases in the training set. Thus, to evaluate the performance of a trained machine learning model, one needs to use data that has not been used for training.

In one embodiment, the collected audio recordings can be divided equally between the training set and the testing set. The machine learning model is trained using the training set and its performance is evaluated using the testing set. The machine learning model is considered to be generalized or well-trained if its performance on the testing set is within a desired range (error) of the performance on the training set. If the performance on the testing set is worse than the training set (the difference in error between the training set and the testing set is greater than a predefined threshold), a two-stage validation and testing approach may be used. The model's accuracy (error) is measured using standard metrics such as Word Error Rate (WER), Character Error Rate (CER), and Sentence Error Rate (SER).

In some embodiments, in a two-stage validation and testing approach, the collected audio recordings are divided between the training set, the validation set, and the testing set. The machine learning model is first trained using the training set, then its parameters are adjusted to improve the model's accuracy and generalization using the validation set, and, finally, the trained machine learning model is tested using the testing set.

In some embodiments, the data set may be divided equally between the desired training, validation, or testing sets. This works well when there is a large collection of data to draw from. In cases where the collection of data samples is limited, other well-known techniques, such as leave one out cross validation and testing or k-fold cross validation may be used to perform validation and testing. Cross-validation is a resampling procedure used to evaluate machine learning models on a limited data sample. The procedure has a single parameter called k that refers to the number of groups that a given data set is to be split into. As such, the procedure is often called k-fold cross-validation. When a specific value for k is chosen, such as k=10, the procedure becomes 10-fold cross-validation.

Cross-validation is primarily used to estimate how the trained model is expected to perform in general when used to make predictions on data not used during the training of the model. The dataset is shuffled randomly and divided into a predefined number (k) of groups. The training and testing process is performed k times, with one of the groups of data being held out as the testing set for each iteration and the remaining k−1 groups being used as the training set. Each model is fitted (trained) on the training set and evaluated (tested) on the test set to determine the level of generalization of the trained models.

Cross validation can help determine the model structure and the parameter training process for the machine learning model. For example, a neural network model can have one or more "hidden" layers of neurons between the input layer and the output layer. Further, different neural network models can be built with different numbers of neurons in the hidden layers and the output layers. In some embodiments, in the training phase, a plurality of machine learning models, such as neural network models having different numbers of layers and different numbers of neurons in each layer, are generated. Each of the plurality of machine learning models is trained using k-fold cross validation. The model (number of layers and number of neurons in each layer) having the highest predictive score is selected.

It is obvious to one of ordinary skill in the art that the machine learning model is not limited to neural networks, and other machine learning models, such as a Markov random field network, support vector machine, random forest of decision trees, or k-nearest neighbor, or a combination of different types of machine learning models may be used as the machine learning model for the speech transcription model 1050 in the dictation module 210.

In some embodiments, the video and image capture logging module 220 automatically extracts and tags (annotates) salient video clips and images of the surgical procedure for inclusion in the operative report. In some embodiments of the invention, the video and image capture logging module 220 receives the written text (transcribed speech) from the dictation module 210 in real time, identifies keywords in the written text, and extracts and annotates video clips or images from a real time video feed of the surgery based on the identified keywords. The annotations may include a time stamp or the keywords that triggered the capturing of the video clips or images.

In some embodiments, the keywords may be predefined commands—such as "take snapshot", "begin clip" and "end clip"—that explicitly instruct the video and image capture logging module 220 to capture a video clip or an image. When the surgeon wants the operative record generation system 200 to record an image, they can utter the words "take snapshot". The dictation module 210 transcribes the speech into text in real time. The video and image capture logging module 220 receives the written text corresponding to the surgeon's dictation, recognizes the predefined keyword "take snapshot", accesses a video feed of the surgery, and records an image at the time corresponding to the dictated command ("take snapshot") by the surgeon. The processing happens in real time, which means the snapshot from the video feed is captured instantaneously with the utterance of the command by the surgeon. The video feed can also have a "preview" window where the past few seconds of video feed are recorded, to ensure that the appropriate video clip or image, at the time the command was given, is recorded. Similarly, the surgeon can use the verbal commands "begin clip" and "end clip" to instruct the operative record generation system 200 to record a video clip of a salient portion of the surgery. The video and image capture logging module 220 records and stores the video clips and images based on the dictated commands in a storage associated with the operative record generation system 200. The operative record creation module 230 accesses the stored video clips and images for generating the operative record 600.

In some embodiments, the keywords may be obtained from predefined templates associated with various surgical procedures. For example, an operative record template for an appendectomy may include keywords or key phrases that describe salient aspects of the surgical procedure. For example, the surgeon may utter the phrase "suprapubic port" when placing a port into the patient's suprapubic region, the phrases "visualizing mesoappendix" and "grasping mesoappendix" when they can see the appendix through a scope and grasp the appendix with forceps, "removing appendix" when they cut the appendix and place it in an endobag, etc. As with the previous embodiments, the dictation module 210 transcribes the speech into text in real time. The system 200 can use these keywords and phrases to automatically record video clips and images, from the video feed of the surgery. This allows a more natural feel during the surgery, where the surgeon can dictate what they are doing rather than commands for instructing the system 200 to record video clips or images. The video and image capture logging module 220 records and stores the video clips and images based on the recognized keywords or phrases in the storage associated with the operative record generation system 200. The operative record creation module 230 accesses the stored video clips and images for generating the operative record 600.

Figure 11:
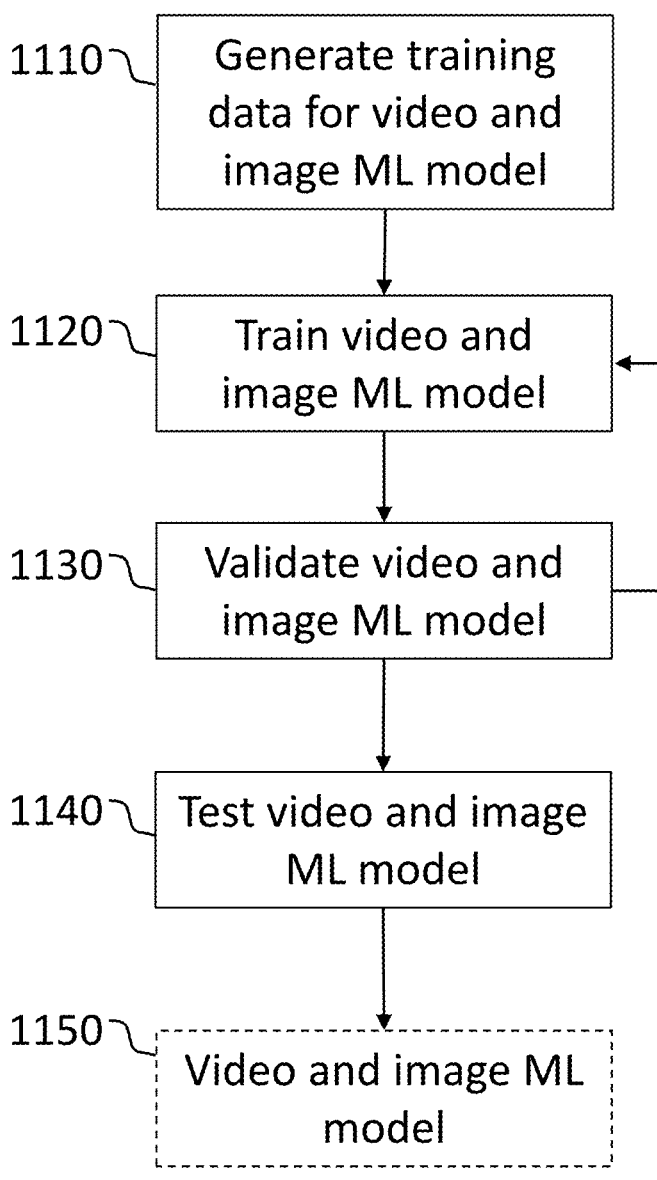
FIG. 11 shows a flowchart of a method of generating a video and image machine learning model, according to some embodiments of the present invention.

FIG. 11 shows a flowchart for an exemplar method 1100 of generating a video and image extraction machine learning model 1150. In some embodiments, the video and image capture logging module 220 includes a video and image extraction machine learning model 1150 that is trained on a large collection of annotated operative reports, to automatically capture video clips and images from the video feed of the surgery without user prompt or intervention. Similar machine learning techniques and models, as those described above with respect to the dictation module 210, may be used to train the video clip and image extraction model 1150 that recognizes salient portions of the video feed of the surgery, and automatically captures the video clips and images, even in a case where the surgeon does not provide any verbal commands, keywords, or phrases. In some embodiments, in step 1110, various visual features are computed from the video clips and images included in the collection of operative reports (the training data set). Commonly used types of features, extracted from images and videos, include colorbased features, texture-based features, shape-based features, and motion-based features. Operative reports may include other features, besides the images and videos, that may be used to learn when the video and image capture logging module 220 should record images and videos, for example, timestamps and starting/ending of various procedures.

In some embodiments, in step 1120, the video and image features, and other features extracted from the operative records 600, are used as training data to train a machine learning model that can monitor the video feed of the surgery, recognize when the video feed is showing a salient portion of the surgery based on the trained model, and automatically record a video clip or an image. In steps 1130 and 1140, respectively, validation and testing of the trained video and image model 1150 is performed. The methods for training, validating, and testing the machine learning model, to be used as the video clip and image extraction model 1150, are similar to those used for training, validating, and testing the speech transcription machine learning model described above. In some embodiments, different video clip and image extraction models (machine learning models) may be trained for different types of surgeries, using only operative records 600 for the corresponding surgeries as training data, to provide increased accuracy and specificity for different surgery types. In some embodiments, a combination of a generalized model and surgery specific models may be used for extracting salient video clips and images.

In some embodiments, the video clip and image extraction model 1150 may be used in stand-alone mode, without receiving any transcription from the dictation module 210, to automatically extract salient video clips and images from the live feed of the surgery. In other embodiments, the video clip and image extraction model 1150 may work in conjunction with commands or phrases recognized by the dictation module 210 to augment the video clips and images recorded in response to the surgeon's dictation. The video and image capture logging module 220 may store video clips and images recorded based on transcribed speech with a different tag, or in a different location, than video clips and images automatically recorded using the trained video clip and image extraction model 1150.

Figure 4:
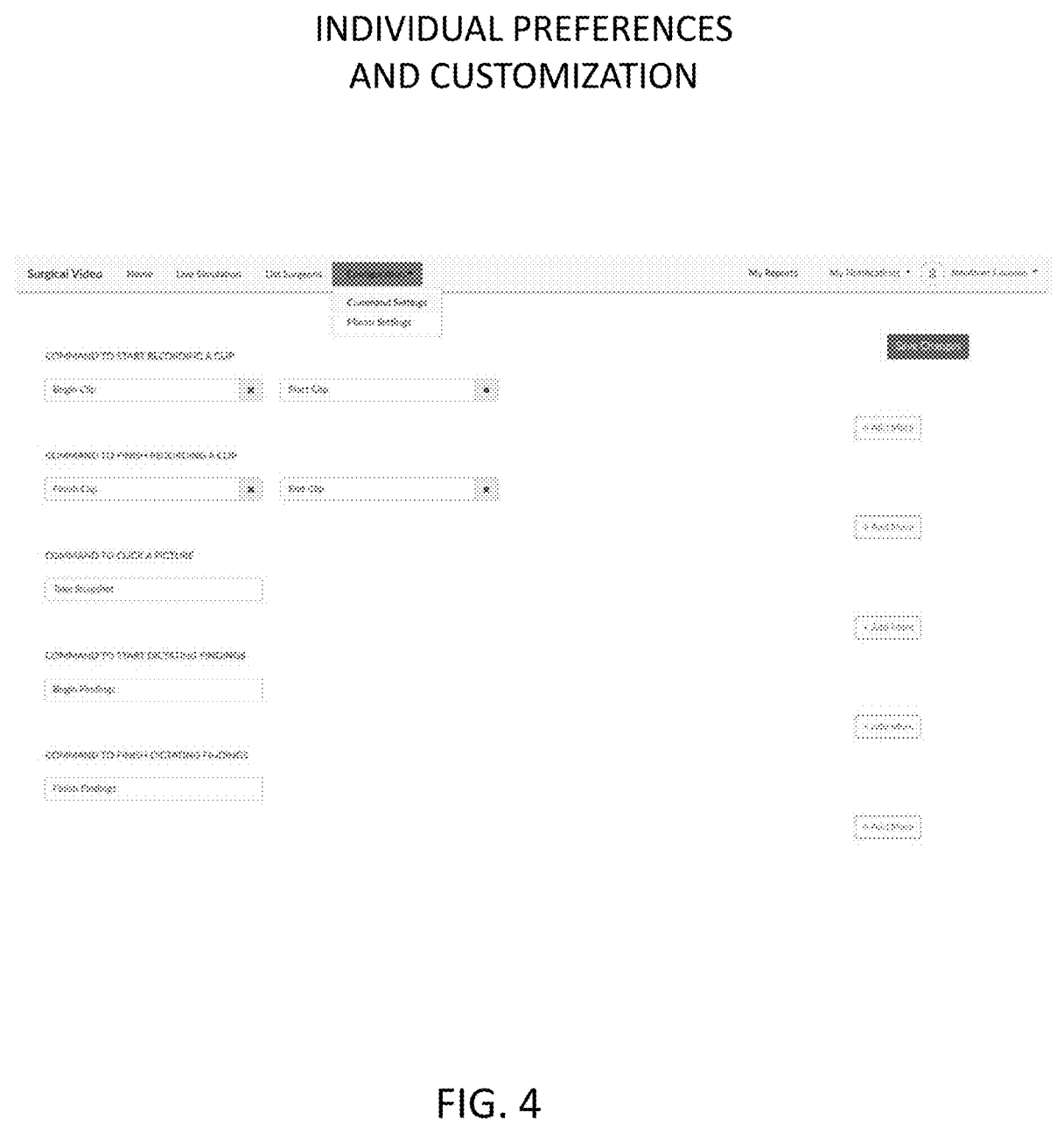

FIG. 4 shows an exemplar user interface screen, displayed on the user interface 250, for the operative record generation system 200, according to some embodiments of the present invention. In some embodiments, user interface screens can be used to set various features that customize the user's interactions with the hardware, the operating environment of the system 200, the manner of interacting with the system 200, the library of macros, the template for the operative report 600, the electronic medical record (EMR), and other metadata and media to be added to the operative report 600. In some embodiments, the customizable hardware interactions include system activation, voice-based interaction during procedure, system de-activation/pause/suspend mode, integration with multiple video and imaging sources, integration with robotic equipment, and integration with existing surgical environment/systems. The software environment customizations include user-based preferences, customizable templates for dictation and report generation, user voice recognition, user accent recognition and definition, and noise cancellation or disregarding of non-user voice/noise. The customizable commands include user preferred commands for system interaction and a standard library that can be modified. The customizable macro library includes user and surgery specific templates of macros and associated content, customizable macros and content based on institution or surgeon, ability to import macros and content.

In some embodiments, the operative report template can be customized to the institution. The library may include multiple templates that can be customized, for example, using logo/institution-based layout, to follow institution-based workflow/content flow customization, or support multiple output formats (csv, word, pdf, xml). The electronic medical record can be customized to include EMR specific API's to fetch data, EMR specific API's to transmit data and formatted content, and API management functions to allow for communication completion.

In some embodiments, the operative record generation system 200 can also include other media and metadata to enrich the surgeon's dictated notes. For example, the system 200 can be customized to permit input of various media within the operative report 600 and workflow, such as the ability to add images and snapshots to reports, the ability to add videos to the report 600, the ability to add voice content to the report 600. Other customizations include the ability to edit/manage report content, the ability to provide voice commands for report formatting and content input, support for multiple report formats available based on templates loaded into the system 200, the ability to send content and report to various sources, the ability to share the report 600 securely with other staff and third party systems and personnel, generating workflow for task management, and reporting status maintenance.

In some embodiments, the operative record generation module 230 performs an exemplar workflow, as shown in FIGS. 5A-5D, to generate the operative report 600. The workflow includes several steps. In a first step, a consent discussion with the patient is recorded. During the consent discussion, a full discussion of risks, benefits, and rationale of the intended procedure is conducted with the patient prior to starting the surgical procedure, and informed consent of the patient or their representative is obtained and recorded. In the next step, initial patient entry into the operative report 600 is performed. After the patient is brought into the surgical venue, the patient identity is confirmed. Other optional information, such as the placement of the patient on the operating table, and securing of the patient to the operating table, are recoded. For example, the patient may have been placed on the operating table in the supine position and all pressure points may have been padded. Serial compression devices may have been placed on the lower extremities. These observations are recorded during the initial patient entry step.

In some embodiments of the invention, in the next step, pre-operative procedures are recorded. For example, a patient may be administered with anesthesia, pre-operative antibiotics, or other medications. The site of the operation may be marked and confirmed. Availability of imaging studies and other diagnostic information required to perform the surgery may be confirmed and recorded.

Once pre-operative procedures are completed, recording of the surgery begins. In some embodiments of the invention, various surgical procedures may be recorded in the operative record generation system 200. In some embodiments of the invention, the operative record generation system 200 includes a plurality of templates associated with various surgical procedures. For example, a thymectomy induction template may be used to record a surgical procedure where, after induction of general endotracheal anesthesia, appropriate access and monitoring lines were placed by the anesthesia team, a double lumen bronchial blocker was placed and its position confirmed with fiberoptic bronchoscopy, and left lung isolation was instituted. As another example, a thymectomy positioning template may be used to record a surgical procedure where the patient was placed in the right hemi-lateral decubitus position with the left side up after confirming operative laterality, all appropriate pressure points were padded, and the patient was prepped and draped in the usual sterile fashion after marking incision sites. As another example, a port placement template may be used to record a surgical procedure where Incision sites were marked and the initial robotic port placed under direct vision with the optical separator trocar, pneumothorax was instituted with CO2 insufflation at a pressure of 8 mmHg, the remaining instrument ports were placed under direct vision, the robotic cart was brought in and attached to the ports, and all instruments were brought in under direct vision.

Upon completion of a surgical procedure, a verification and attestation step may be used to confirm that sponge, needle, and instrument counts were correct prior to closure and there were no intraoperative complications. The primary attending surgeon, or other physician(s), may attest that they were present for the entirety of the procedure and performed or directly supervised all key and non-key portions of the procedure.

The surgeon can also perform real-time editing and finalization of operation report 600. FIG. 5B shows an exemplar user interface screen for review and modification of the initial operative report 600. In some embodiments, the surgeon can review the operative report 600 while in progress or after completion of the surgical procedure. The surgeon can edit the report 600 through keyboard or voice command. Editing of content, images (captions as well as title) and video is also available through the system 200. The surgeon can rearrange, delete, or modify content, images, video and voice commands. The surgeon can also mark specific content as "private", which will only be shared/viewed by specific users. User specific content access can be managed through defined roles and permissions.

In the final step, the generated report 600 is stored, along with annotated/tagged media such as text, voice, images and video, captured by the system 200 during dictation of the procedure by the surgeon. The final report 600, or specific images, videos, voice memo's can be sent to multiple sources or become part of a workflow to allow for securely sharing content.

In some embodiments, one or more of the workflow steps discussed above may be implemented as macros that can be executed using a simple or short command. This way, a surgeon performing the operation could use dictation "short cuts" to record an otherwise long procedure, thereby improving efficiency.

In some embodiments, natural language processing is used for voice capture and input. The workflow also includes capture and intelligent tagging of video and image during the surgical procedure. As discussed with reference to FIG. 4, the system allows hardware, security and workflow customization within an institution.

In some embodiments, video clip capture initiation and termination is managed through voice prompt/command, which is part of the command library. It allows for real-time command execution and timestamping the video clip and storing the exact clip into the system repository. This video clip can be "tagged" with content through voice dictation or keyboard. This can be done in real-time or after the fact.

FIG. 6 shows an exemplar operative record 600 generated by the operative record generation system 200, according to some embodiments. The report 600 (operative record) is generated by collating all of the content, video, voice, and images in a specified format that is determined by the selected template in the system 200. The report generation process identifies "required" content and "optional" content, which is controlled by the surgeon and/or institution and set in the system preferences. The operative report 600 goes through a checklist of items, order of items, and format to generate the final report 600. Everything is timestamped and tagged to allow for validation of user and changes.

Figure 7:
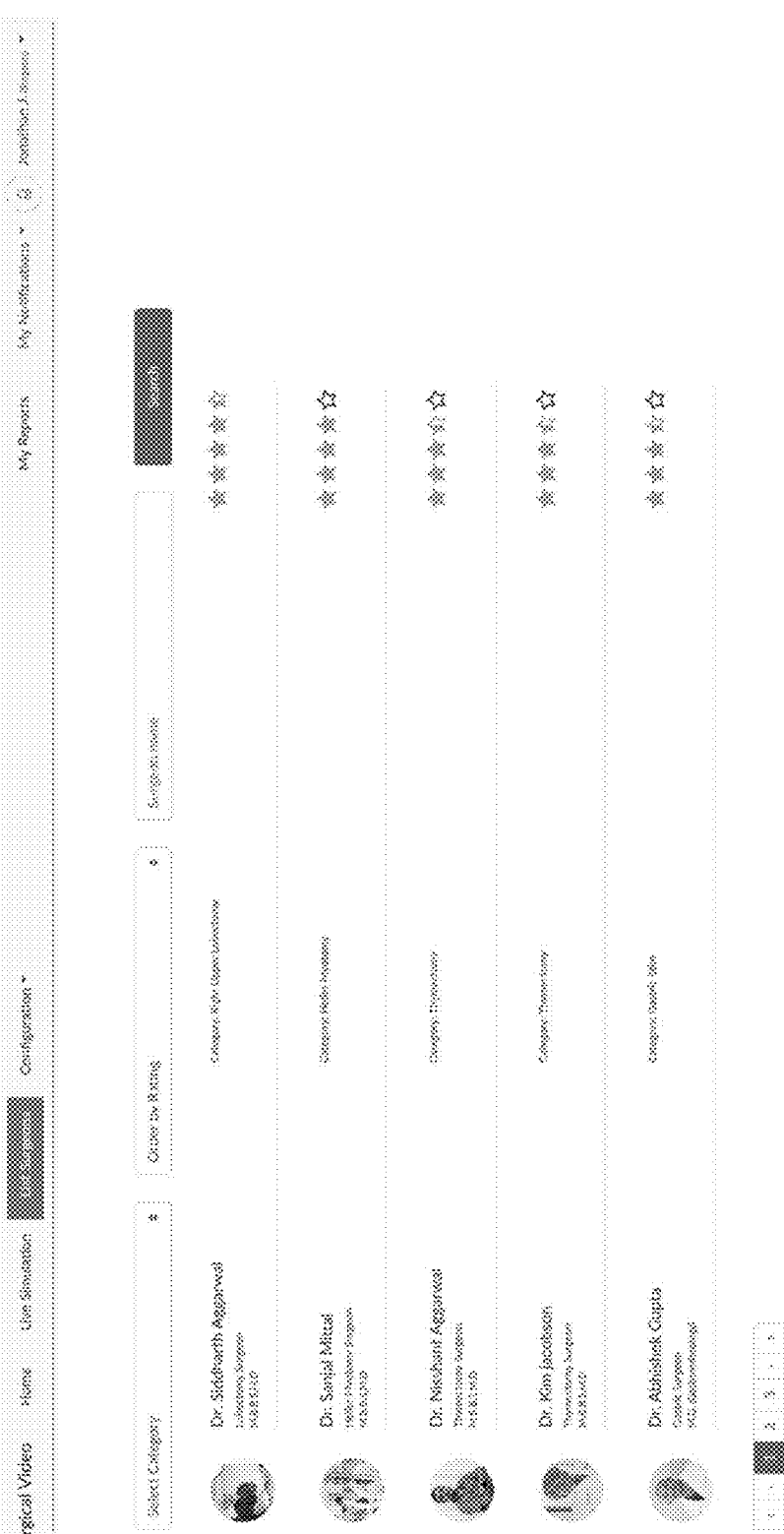
FIG. 7 shows an exemplar user interface for assessing and managing credentials based on operative records generated by the operative record generation system, according to some embodiments of the present invention.

FIG. 7 shows an exemplar user interface 250 for assessing and managing credentials based on operative reports 600 generated by the operative record generation system 200. In some embodiments, video clips captured during a procedure are used to visually assess the surgeon's technical competency through a direct rating scale. These datapoints can used at the discretion of the hospital administration/or appropriate authority for credentialing and certification processes. Videos and associated dictation and voice memo's along with images can be shared with a learning management system or an assessment system. Different users have access to the learning management and assessment systems. In some embodiments, these users have the ability to view and rate the surgical procedure and surgeon competency. In some embodiments, an AI-based scoring system may be used to determine ratings. Ratings are stored securely and a rating report can be generated as a CSV, word, pdf or XML file, which can be printed and/or shared with another system through defined API's.

Figure 8:
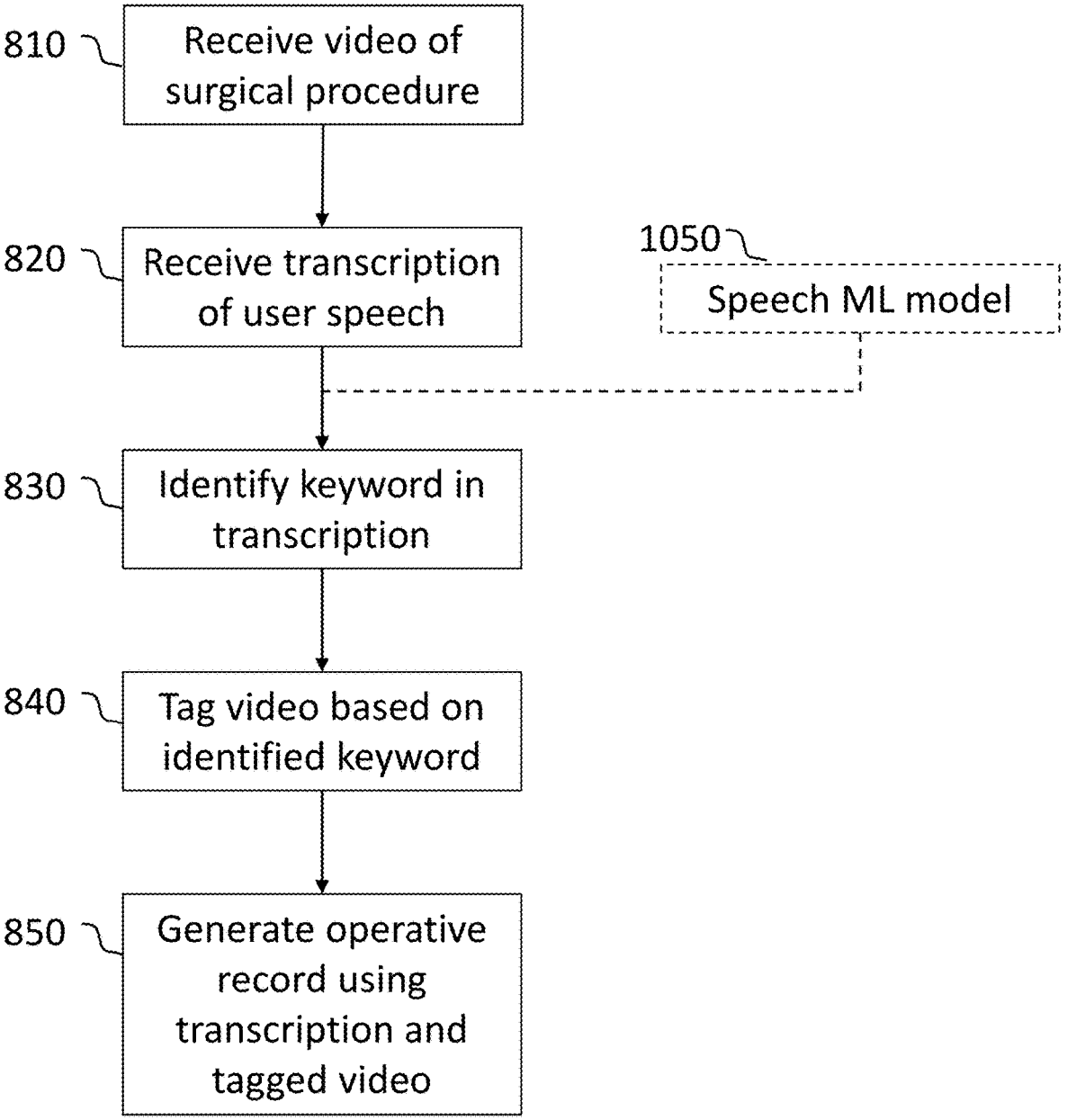
FIG. 8 shows a flowchart of a method of generating an operative record, according to some embodiments of the present invention.

FIG. 8 shows a flowchart for an exemplar method 800 of generating an operative report 600, according to some embodiments. In step 810, a video of the surgical procedure is received in real time and displayed on the user interface 250 of the operative record generation system 200. In step 820, a transcription of the user's (surgeon) speech is received. In step 830, the transcription is analyzed in real time, using the speech ML model 1050, to identify keywords associated with macros and tasks. For example, a keyword in the transcription may be a short-hand for a longer transcript to be added to the operative report 600. As another example, a keyword may trigger capturing images or a video portion of the real time video being displayed on the user interface 250. In step 840, when a keyword that triggers image or video capture is identified in the transcription, the images or video portion is recorded and stored. The images or video portion may be tagged with a timestamp or other metadata extracted from the transcription. In step 850, the operative report 600 is generated using the operative report template, the transcription, and the tagged images or video portions.

Figure 9:
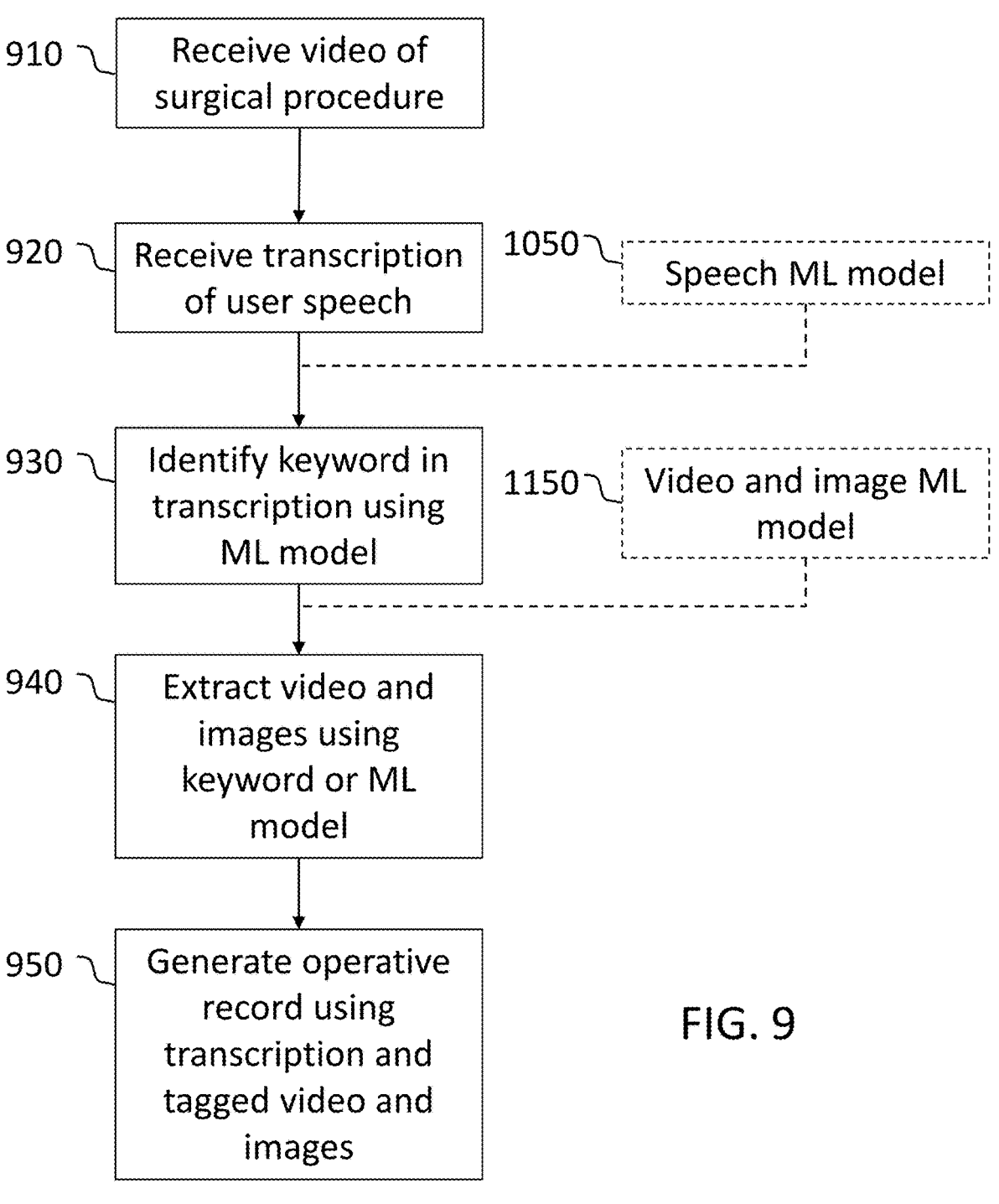
FIG. 9 shows a flowchart of another method of generating an operative record, according to some embodiments of the present invention.

FIG. 9 shows a flowchart for another exemplar method 900 of generating an operative report 600, according to some embodiments. In step 910, a video of the surgical procedure is received in real time and displayed on the user interface 250 of the operative record generation system 200. In step 920, a transcription of the user's (surgeon) speech is received. In step 930, the transcription is analyzed in real time, using the speech ML model 1050, to identify keywords associated with macros and tasks. For example, a keyword in the transcription may be a short-hand for a longer transcript to be added to the operative report 600. As another example, a keyword may trigger capturing images or a video portion of the real time video being displayed on the user interface 250. In step 840, when either a keyword that triggers image or video capture is identified in the transcription or the video and image ML model 1150 determines that the video feed of the surgery is showing a salient aspect of the surgery, the images or video portion is recorded and stored. The images or video portion may be tagged with a timestamp or other metadata extracted from the transcription. In step 850, the operative report 600 is generated using the operative report template, the transcription, and the tagged images or video portions.

In some embodiments, a system for automatic extraction of one or more salient images from a surgical video stream comprises one or more computer accessible-storage devices configured to store instructions and one or more processors communicatively connected to the one or more computer accessible storage devices and configured to execute the stored instructions to receive a plurality of records including annotated images from recorded surgical procedures to use as training data for generating an image extraction machine learning model; extract one or more first features from the training data; generate the image extraction machine learning model, by training the image extraction machine learning model on the extracted one or more first features, to output salient images in the training data; receive the surgical video stream; extract one or more second features from the surgical video stream; and input the one or more second features into the trained image extraction machine learning model to output the one or more salient images from the surgical video stream.

In some embodiments, the system is further configured to automatically generate a surgical operative record including at least the extracted one or more salient images from the surgical video stream.

In some embodiments, the system is further configured to receive a plurality of annotated speech samples to use as training data for generating a speech transcription machine learning model; extract one or more third features from the training data; generate the speech machine learning model, by training the speech machine learning model on the extracted one or more third features, to output a speech transcription; receive an audio stream associated with the surgical video stream; extract one or more fourth features from the audio stream; input the one or more fourth features into the trained speech machine learning model to output a speech transcription of the audio stream; and associate the extracted one or more salient images with the output speech transcription.

In some embodiments, the system is further configured to automatically generate a surgical operative record including at least the one or more extracted salient images and the associated output speech transcription.

In some embodiments, a timestamp is associated with each salient image of the one or more salient images.

In some embodiments, the system is further configured to receive a plurality of records including annotated video clips from recorded surgical procedures to use as second training data for training the image extraction machine learning model; extract one or more fifth features from the second training data; train the image extraction machine learning model, using the extracted one or more fifth features, to output salient video clips in the second training data; extract one or more sixth features from the surgical video stream; and input the one or more sixth features into the trained image extraction machine learning model to output one or more salient video clips from the surgical video stream.

In some embodiments, a processor implemented method of automatically extracting salient images from a surgical video stream comprises receiving a plurality of records including annotated images from recorded surgical procedures to use as training data for generating an image extraction machine learning model; extracting one or more first features from the training data; generating the image extraction machine learning model, by training the image extraction machine learning model on the extracted one or more first features, to output salient images in the training data; receiving the surgical video stream; extracting one or more second features from the surgical video stream; and inputting the one or more second features into the trained image extraction machine learning model to output the one or more salient images from the surgical video stream.

In some embodiments, the method further comprises automatically generating a surgical operative record including at least the extracted one or more salient images from the surgical video stream.

In some embodiments, the method further comprises receiving a plurality of annotated speech samples to use as training data for generating a speech transcription machine learning model; extracting one or more third features from the training data; generating the speech machine learning model, by training the speech machine learning model on the extracted one or more third features, to output a speech transcription; receiving an audio stream associated with the surgical video stream; extracting one or more fourth features from the audio stream; inputting the one or more fourth features into the trained speech machine learning model to output a speech transcription of the audio stream; and associating the extracted one or more salient images with the output speech transcription.

In some embodiments, the method further comprises automatically generating a surgical operative record including at least the one or more extracted salient images and the associated output speech transcription.

In some embodiments, the method further comprises associating a timestamp with each salient image of the one or more salient images.

In some embodiments, the method further comprises receiving a plurality of records including annotated video clips from recorded surgical procedures to use as second training data for generating the image extraction machine learning model; extracting one or more fifth features from the second training data; training the image extraction machine learning model, using the extracted one or more fifth features, to output salient video clips in the second training data; extracting one or more sixth features from the surgical video stream; and inputting the one or more sixth features into the trained image extraction machine learning model to output one or more salient video clips in the surgical video stream.

In some embodiments, an operative record generation system comprises one or more computer accessible-storage devices configured to store instructions and one or more processors communicatively connected to the one or more computer accessible storage devices and configured to execute the stored instructions to provide a plurality of program modules including a user interface, a speech processing module, an image processing module, and a record generation module.

The user interface is configured to display a video of the surgical procedure in a first portion of a screen and a transcription of a user's speech in a second portion of the screen. The speech processing module is configured to identify one or more predetermined keywords in the transcription, each keyword associated with a particular function executed by the operative record generation system. The image processing module is configured to, in a case where the speech processing module identifies a keyword associated with an image capture or video capture function, record an image or a portion of the video of the operation displayed on the screen and a timestamp associated with the recorded image or the portion of the video. The record generation module is configured to generate the operative record using the transcription of the user's speech and the recorded image or the portion of the video.

In some embodiments, the user interface further includes setting screens configured to personalize settings of the speech processing module for a user.

In some embodiments, the user interface is further configured to display an indicator indicating an active or inactive status of the operative record generation system.

In some embodiments, the speech processing module is further configured to extract the user's speech by filtering an input audio stream to remove background noise and non-user speech.

In some embodiments, the video and image processing module is further configured to receive a plurality of operative records including tagged videos and images to use as training data for generating a video and image extraction machine learning model; extract one or more features from the training data; and train the video and image extraction machine learning model, using the extracted one or more features, to automatically record an image or a portion of the video of the operation displayed on the screen and a timestamp associated with the recorded image or the portion of the video.

In some embodiments, the system further includes a speech transcription module configured to receive a plurality of transcribed and annotated speech samples to use as training data for generating a speech transcription machine learning model; extract one or more features from the training data; and train the speech machine learning model, using the extracted one or more features, to transcribe the user's speech.

In some embodiments, a method of generating an operative record includes displaying, on a user interface, a video of the surgical procedure in a first portion of a screen and a transcription of a user's speech in a second portion of the screen; identifying one or more predetermined keywords in the transcription, each keyword associated with a particular function executed by the operative record generation system; in a case where a keyword associated with an image capture or video capture function is identified, recording an image or a portion of the video of the operation displayed on the screen and a timestamp associated with the recorded image or the portion of the video; and generating the operative record using the transcription of the user's speech and the recorded image or the portion of the video.

In some embodiments, the method further includes extracting the user's speech by filtering an input audio stream to remove background noise and non-user speech.

In some embodiments, the method further includes receiving a plurality of operative records including tagged videos and images to use as training data for generating a video and image extraction machine learning model; extracting one or more features from the training data; and training the video and image extraction machine learning model, using the extracted one or more features, to automatically record an image or a portion of the video of the operation displayed on the screen and a timestamp associated with the recorded image or the portion of the video.

In some embodiments, the method further includes receiving a plurality of transcribed and annotated speech samples to use as training data for generating a speech transcription machine learning model; extracting one or more features from the training data; and training the speech machine learning model, using the extracted one or more features, to transcribe the user's speech.

In some embodiments, one or more computer non-transitory storage media are configured to store one or more programs that include instructions for executing one or more of the various methods discussed above.

Subsets or combinations of various embodiments described above provide further embodiments. These and other changes can be made to the invention in light of the above-detailed description and still fall within the scope of the present invention. In general, in the following claims, the terms used should not be construed to limit the invention to the specific embodiments disclosed in the specification. Accordingly, the invention is not limited by the disclosure, but instead its scope is to be determined entirely by the following claims.

The invention claimed is:

1. A system for automatic extraction of one or more salient images from a surgical video stream, comprising:
   one or more computer accessible-storage devices configured to store instructions; and
   one or more processors communicatively connected to the one or more computer accessible storage devices and configured to execute the stored instructions to:
      receive a plurality of records including annotated images from recorded surgical procedures to use as training data for generating an image extraction machine learning model;
      extract one or more first features from the training data;
      generate the image extraction machine learning model, by training the image extraction machine learning model on the extracted one or more first features, to output salient images in the training data;
      receive the surgical video stream in real time during a surgical procedure;
      extract one or more second features from the surgical video stream;
      in a first operation mode:
         input the one or more second features into the trained image extraction machine learning model to output first salient images from the surgical video stream in real time without user intervention; and
         tag the first salient images with a first identifier indicating automatic extraction; and
      in a second operation mode:
         receive an audio stream from a surgeon in real time during the surgical procedure;
         transcribe the audio stream in real time to generate transcribed text;
         identify one or more predetermined keywords in the transcribed text from a predefined template associated with a type of surgical procedure being performed, wherein the keywords describe salient procedural aspects of the surgical procedure;
         input the one or more second features into the trained image extraction machine learning model to output second salient images from the surgical video stream in response to identifying the keywords; and
         tag the second salient images with a second identifier indicating keyword-triggered extraction.

2. The system according to claim 1, wherein the one or more processors are further configured to automatically generate a surgical operative record including at least the extracted first salient images and the second salient images from the surgical video stream.

3. The system according to claim 1, wherein the one or more processors are further configured to:

receive a plurality of annotated speech samples to use as training data for generating a speech transcription machine learning model;

extract one or more third features from the training data;

generate the speech transcription machine learning model, by training the speech transcription machine learning model on the extracted one or more third features, to output a speech transcription;

extract one or more fourth features from the audio stream; and input the one or more fourth features into the trained speech machine learning model to output the transcribed text.

4. The system according to claim 3, wherein the one or more processors are further configured to automatically generate a surgical operative record including at least the extracted second salient images and the associated transcribed text.

5. The system according to claim 1, wherein a timestamp is associated with each salient image of the first salient images and the second salient images.

6. The system according to claim 1, wherein the one or more processors are further configured to:

receive a plurality of records including annotated video clips from recorded surgical procedures to use as second training data for training the image extraction machine learning model;

extract one or more fifth features from the second training data;

train the image extraction machine learning model, using the extracted one or more fifth features, to output salient video clips in the second training data;

extract one or more sixth features from the surgical video stream; and input the one or more sixth features into the trained image extraction machine learning model to output one or more salient video clips from the surgical video stream.

7. A processor implemented method of automatically extracting salient images from a surgical video stream, comprising:

receiving a plurality of records including annotated images from recorded surgical procedures to use as training data for generating an image extraction machine learning model;

extracting one or more first features from the training data;

generating the image extraction machine learning model, by training the image extraction machine learning model on the extracted one or more first features, to output salient images in the training data;

receiving the surgical video stream in real time during a surgical procedure;

extracting one or more second features from the surgical video stream;

in a first operation mode:

inputting the one or more second features into the trained image extraction machine learning model to output first salient images from the surgical video stream in real time without user intervention; and tagging the first salient images with a first identifier indicating automatic extraction; and in a second operation mode:

receiving an audio stream from a surgeon in real time during the surgical procedure;

transcribing the audio stream in real time to generate transcribed text;

identifying one or more predetermined keywords in the transcribed text from a predefined template associated with a type of surgical procedure being performed, wherein the keywords describe salient procedural aspects of the surgical procedure;

inputting the one or more second features into the trained image extraction machine learning model to output second salient images from the surgical video stream in response to identifying the keywords; and tagging the second salient images with a second identifier indicating keyword-triggered extraction.

8. The method according to claim 7, further comprising automatically generating a surgical operative record including at least the extracted first salient images and the second salient images from the surgical video stream.

9. The method according to claim 7, further comprising:

receiving a plurality of annotated speech samples to use as training data for generating a speech transcription machine learning model;

extracting one or more third features from the training data;

generating the speech transcription machine learning model, by training the speech transcription machine learning model on the extracted one or more third features, to output a speech transcription;

extracting one or more fourth features from the audio stream; and inputting the one or more fourth features into the trained speech machine learning model to output the transcribed text.

10. The method according to claim 9, further comprising automatically generating a surgical operative record including at least the extracted second salient images and the associated transcribed text.

11. The method according to claim 7, further comprising associating a timestamp with each salient image of the first salient images and the second salient images.

12. The method according to claim 7, further comprising:

receiving a plurality of records including annotated video clips from recorded surgical procedures to use as second training data for generating the image extraction machine learning model;

extracting one or more fifth features from the second training data;

training the image extraction machine learning model, using the extracted one or more fifth features, to output salient video clips in the second training data;

extracting one or more sixth features from the surgical video stream; and inputting the one or more sixth features into the trained image extraction machine learning model to output one or more salient video clips in the surgical video stream.

13. A computer non-transitory storage medium configured to store a program for a method of automatically extracting salient images from a surgical video stream, the method comprising:

receiving a plurality of records including annotated images from recorded surgical procedures to use as training data for generating an image extraction machine learning model;

extracting one or more first features from the training data;

generating the image extraction machine learning model, by training the image extraction machine learning model on the extracted one or more first features, to output salient images in the training data;

receiving the surgical video stream in real time during a surgical procedure;

extracting one or more second features from the surgical video stream;

in a first operation mode:

inputting the one or more second features into the trained image extraction machine learning model to output first salient images from the surgical video stream in real time without user intervention; and tagging the first salient images with a first identifier indicating automatic extraction; and in a second operation mode:

receiving an audio stream from a surgeon in real time during the surgical procedure;

transcribing the audio stream in real time to generate transcribed text;

identifying one or more predetermined keywords in the transcribed text from a predefined template associated with a type of surgical procedure being performed, wherein the keywords describe salient procedural aspects of the surgical procedure;

inputting the one or more second features into the trained image extraction machine learning model to output second salient images from the surgical video stream in response to identifying the keywords; and tagging the second salient images with a second identifier indicating keyword-triggered extraction.

14. The storage medium according to claim 13, wherein the method further comprises automatically generating a surgical operative record including at least the extracted first salient images and the second salient images from the surgical video stream.

15. The storage medium according to claim 13, wherein the method further comprises:

receiving a plurality of annotated speech samples to use as training data for generating a speech transcription machine learning model;

extracting one or more third features from the training data;

generating the speech transcription machine learning model, by training the speech transcription machine learning model on the extracted one or more third features, to output a speech transcription;

extracting one or more fourth features from the audio stream; and inputting the one or more fourth features into the trained speech machine learning model to output the transcribed text.

16. The storage medium according to claim 15, wherein the method further comprises automatically generating a surgical operative record including at least the extracted second salient images and the associated transcribed text.

17. The storage medium according to claim 13, wherein the method further comprises associating a timestamp with each salient image of the first salient images and the second salient images.

18. The storage medium according to claim 13, wherein the method further comprises:

receiving a plurality of records including annotated video clips from recorded surgical procedures to use as second training data for generating the image extraction machine learning model;

extracting one or more fifth features from the second training data;

training the image extraction machine learning model, using the extracted one or more fifth features, to output salient video clips in the second training data;

extracting one or more sixth features from the surgical video stream; and inputting the one or more sixth features into the trained image extraction machine learning model to output one or more salient video clips in the surgical video stream.

* * * * *